United States Patent [19]

Heckele et al.

[11] Patent Number: 5,520,678
[45] Date of Patent: May 28, 1996

[54] MANIPULATOR ARM WITH PROXIMAL AND DISTAL CONTROL BALLS

[75] Inventors: Helmut Heckele, Knittlingen; Friederich Hähnle, Bretten, both of Germany

[73] Assignee: Richard Wolf GmbH, Knittlingen, Germany

[21] Appl. No.: 346,776

[22] Filed: Nov. 30, 1994

[30] Foreign Application Priority Data

Nov. 30, 1993 [DE] Germany .......................... 43 40 707.2

[51] Int. Cl.$^6$ .................................................. A61B 19/00
[52] U.S. Cl. .................................................. 606/1; 606/205
[58] Field of Search .................................. 600/141, 142, 600/149, 201, 225, 229; 606/1, 119, 198, 205–211

[56] References Cited

U.S. PATENT DOCUMENTS

| | | | |
|---|---|---|---|
| 1,382,783 | 6/1921 | Howard | 600/229 |
| 2,608,192 | 8/1952 | Heitmeyer et al. | 600/229 |
| 5,025,778 | 6/1991 | Silverstein et al. | |
| 5,382,252 | 1/1995 | Failla et al. | 606/119 |
| 5,405,344 | 4/1995 | Williamson et al. | 606/1 |

FOREIGN PATENT DOCUMENTS

| | | |
|---|---|---|
| 219814 | 3/1908 | Germany . |
| 650368 | 9/1937 | Germany . |
| 2379848 | 9/1978 | Germany . |
| 3707450A1 | 3/1987 | Germany . |
| 4213426 | 10/1992 | Germany . |
| 4136861A1 | 5/1993 | Germany . |
| 93/07816 | 4/1993 | WIPO . |

Primary Examiner—Stephen C. Pellegrino
Assistant Examiner—Glenn Dawson
Attorney, Agent, or Firm—Cohen, Pontani, Lieberman, Pavane

[57] ABSTRACT

A surgical manipulator arm has a first and a second control ball rotatably mounted and disposed at a proximal end and a distal end of an outer-shaft tube, respectively. The control balls are coupled to each other through coupling elements such, for example, as control wires so that rotational movements of the first control ball can be transmitted correspondingly to the second control ball or vice versa. The manipulator arm has an actuator portion connected to the first control ball and a follower portion connected to the second control ball for selectively and detachably mounting a handling part and an effector part of an instrument. The first and second control balls are mounted in such a way so as to permit their respective actuator and follower portions to rotate and pivot about the longitudinal axis of the outer-shaft tube. The central bore defines a connective passage from the actuator portion, through the outer-shaft tube, and to the follower portion. The connective passage thus formed allows a user to insert a flexible surgical instrument therethrough.

17 Claims, 3 Drawing Sheets

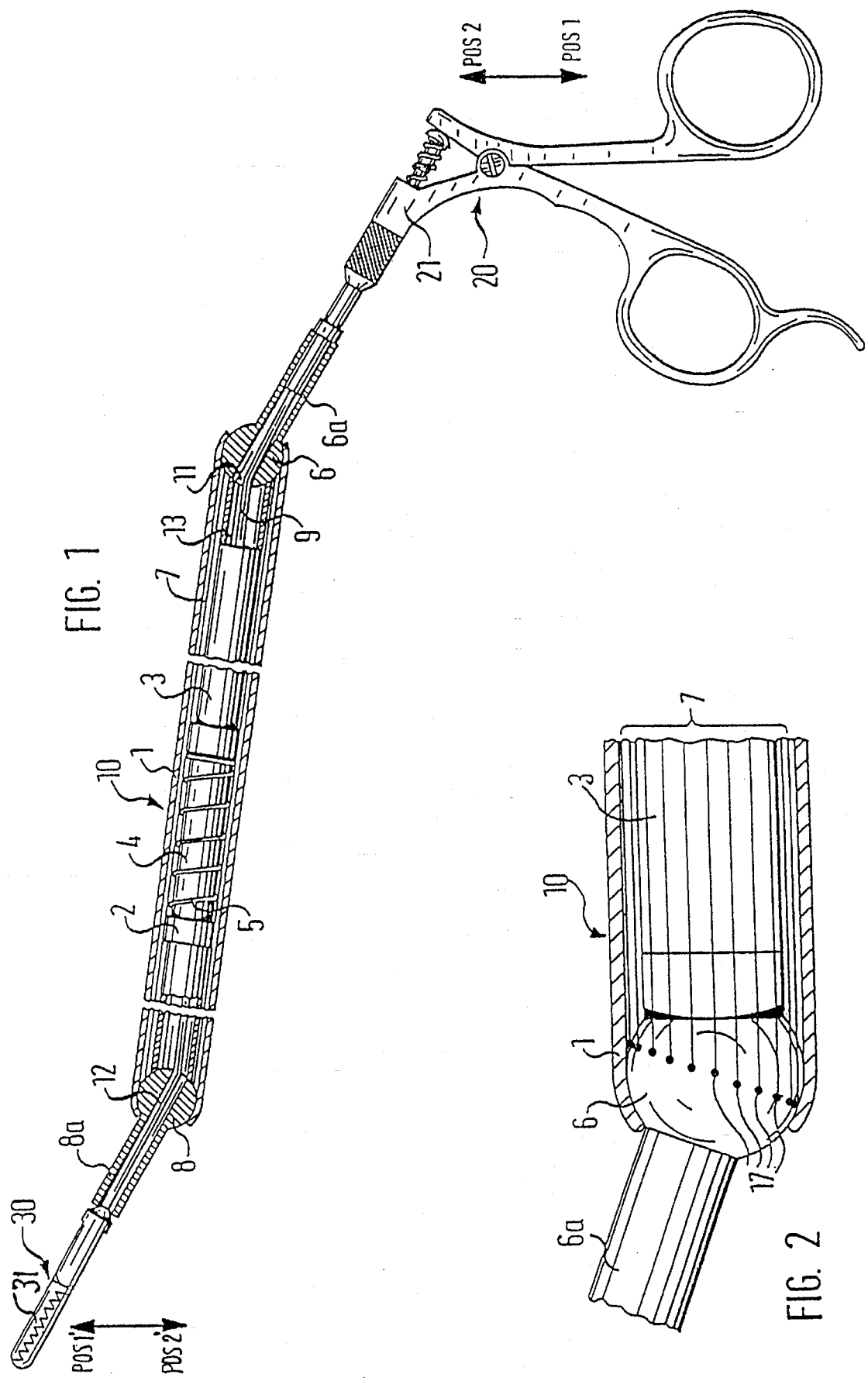

MANIPULATOR ARM WITH PROXIMAL AND DISTAL CONTROL BALLS

BACKGROUND OF THE INVENTION

1. Field of the Invention

The present invention relates to surgical manipulators and, more particularly, a surgical manipulator arm having a first and second control ball rotatably mounted at opposite ends thereof and directly coupled to each other for corresponding rotational and pivotal movements.

2. Description of the Prior Art

Surgical or diagnostic procedures of the invasive types are usually, and justifiably, a choice of last resort for both the patient and his doctor. One reason is that such procedures are traumatic to the patients and thus necessitating the administration of expensive anesthetics—local or, even, general. Another reason is that complications such as infections may ensue, thereby making post-operative care critically important.

Having mentioned some of the drawbacks of invasive procedures, one appreciates the value of surgical techniques known as minimally invasive procedures. These procedures recognize the fact that at times invasive surgical or diagnostic procedures are inevitable. However, the trauma or associated complications can be dramatically reduced if the size of the incision in the epidermis is kept to a minimum such, for example, as the size of a keyhole. To that end, an instrument which enables precise maneuvering of a small device inserted through such an incision in the epidermis is highly desirable.

German patent publication DE-A-41 36 861 discloses a surgical manipulator for minimally invasive surgeries. The surgical manipulator has a handling part at its proximal end and a movable effector located at its distal end. A user may control the movement of the effector by manipulating the handling part with one hand. The publication further discloses that the effector can be controlled via a torsion-proof wire piece or tube.

There have been suggested numerous systems for controlling movements of the effector such, for example, as pneumatic, hydraulic, piezoelectric, magnetostrictive and electromotive control systems. However, none discusses in details the types of effector movement possible with the various control regimes.

Therefore, it is an object of the present invention to provide a surgical manipulator arm with a simple and precise mechanical linkage system so that a user can manipulate a small surgical device attached to the manipulator arm for movement within a bodily cavity. Another object of the invention is to provide a light weight and economically efficient surgical manipulator arm.

SUMMARY OF THE INVENTION

The present invention provides a surgical manipulator arm having a first and a second control ball rotatably mounted and disposed substantially within a proximal and distal end of an outer-shaft tube, respectively. The control balls are coupled to each other through one or more coupling elements such that movements of the first control ball are correspondingly transmitted to the second control ball or vice versa. The manipulator arm has a central bore or connective passage therethrough so that an instrument such, for example, as an endoscope, may be inserted.

The manipulator arm, in accordance with a feature of the present invention, has an actuator portion connected to the first control ball and a follower portion connected to the second control ball for selectively and detachably connecting a handling part and an effector part of an instrument, respectively. The first control ball is mounted within the outer-shaft tube in such a way so as to permit the actuator portion to rotate and pivot about the longitudinal axis of the outer-shaft tube. The second control ball is similarly mounted in the outer-shaft tube so that the follower portion can also rotate and pivot about the longitudinal axis of the outer-shaft tube.

The control balls advantageously provide bedding, i.e. attachment areas for the coupling elements. Areas of the control balls which do not serve as bedding may take on nonspherical forms.

In accordance with a preferred embodiment of the present invention, coupling elements are provided for establishing a non-positive mechanical connection between the control balls. The non-positive connection permits the control balls to pivot and rotate in a controlled, coupled manner so that the movements of a user imparted to the actuator portion are accurately and directly transmitted to the follower portion. By comparison, indirectly operated power transmission systems generally do not provide this advantage. Moreover, indirectly operated power transmission systems are typically heavier and more costly to produce.

In accordance with another preferred embodiment of the present invention, the coupling elements are made up of a plurality of control wires with each end of a control wire attached, preferably, equidistantly, to corresponding points on and around the peripheral surfaces of the control balls. Each wire is pre-tensioned so as to permit a very taut, direct and play-free coupling of the rotational movements of the control balls. Preferably, spacer tubes are positioned between the first and second control ball and spaced annularly within the connective passage of the outer-shaft tube. The spacer tubes hold the two control balls in a spaced relationship such that the control wires remain taut and tight irrespective of whether the control balls are in motion or at rest.

Preferably, the manipulator arm has two outer spacer tubes positioned within the outer-shaft tube, each outer spacer tube being disposed proximate each control ball. The outer spacer tubes are resiliently spaced apart by a compressed coil spring. An inner spacer tube is slidably received and annularly spaced within the outer spacer tubes and the coil spring.

In accordance with another feature of the present invention, the manipulator arm provides peripheral recesses in the spacer tubes for guiding the control wires. Preferably, the peripheral recesses in the spacer tubes are equidistant along the longitudinal direction of the spacer tubes. The control balls are thus linked to each other through the control wires in an equidistant manner. To facilitate the attachment of a medical instrument to the manipulator arm, the actuator portion and the follower portion may be provided with tube-like extensions.

Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

BRIEF DESCRIPTION OF THE DRAWINGS

In the drawings, wherein like reference characters denote similar elements throughout the several views:

FIG. 1 is a side sectional view of an embodiment of the manipulator arm with an exemplary flexible forceps attached to the follower portion and an exemplary handling part secured to the actuator portion;

FIG. 2 is an enlarged view of the control ball of FIG. 1 with control wires attached thereto;

DETAILED DESCRIPTION OF PRESENTLY PREFERRED EMBODIMENTS

Figure 3:
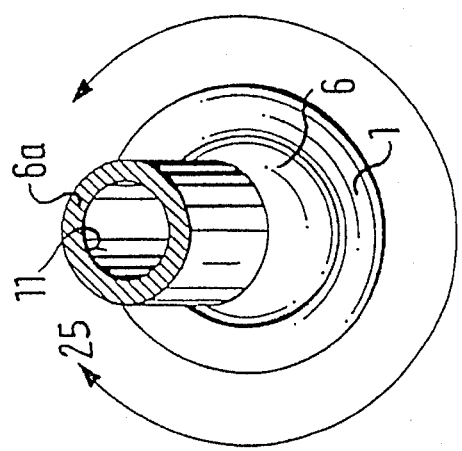
FIG. 3 is a perspective view of the control ball with the follower portion of FIG. 1 illustrating rotational and pivotal movements thereof.

As can be seen in FIG. 1, the manipulator arm 10, in accordance with a preferred embodiment of the present invention, advantageously transmits movements from a handling part 20 of an instrument such, for example, as a flexible forceps to an effector part 30 of the instrument. The exemplary flexible forceps shown in FIG. 1 has a scissor-like handle 21, a claw-like effector 31 and a flexible shaft 9, which runs through a connective passage 11, 12, 13 in the manipulator arm 10. At a proximal end of the manipulator arm 10 there is a first control ball 6 connected to an actuator portion 6a for selectively and detachably mounting the handling part 20. The actuator portion 6a is preferably shaped as a tube extension. At a distal end of the manipulator arm 10 there is a second control ball 8 connected to a follower portion 8a. Similar to the actuator portion 6a, the follower portion 8a is preferably shaped as a tube extension for selectively and detachably securing an effector part 30. The manipulator arm 10 has an outer-shaft tube 1 spanning substantially from the first control ball 6 to the second control ball 8 and substantially covering thereof.

Spaced annularly within the outer-shaft tube 1 of the manipulator arm 10 are outer-spacer tubes 2 and 3 which are disposed proximate the first and second control balls 8 and 6, respectively. The first and second control balls 8 and 6 are coupled through coupling elements such, for example, as control wires 7. An inner spacer tube 4 is slidably and axially received and annularly positioned within the outer spacer tubes 2 and 3. A coil spring 5, being interposed and compressed between confronting ends of the outer spacer tubes 2 and 3 and slidably received over the inner spacer tube 4, pre-tensions the control wires 7 by resiliently urging the two outer spacer tubes 2 and 3 axially and against the control balls 8 and 6, respectively.

The control balls 6 and 8 have central bores 11 and 12, respectively, which are in substantial alignment with the passageways in the actuator portion 6a and follower portion 8a. The actuator 6a and follower portions 8a, which have the functions of selectively and detachably securing an instrument, may be formed as tube-like extensions. The connective passage from the actuator portion 6a to the follower portion 8a is so defined such that a flexible element 9 for transmitting movements of the handling part 20 to the effector part 30 may be inserted therethrough.

As shown in FIG. 2 and as described above, the first control ball 6 and the second control ball 8 are mechanically coupled to one another via coupling elements such, for example, as multiple control wires 7. The attachment points 17 on the control balls 6 and 8 for control wires 7 are illustrated only schematically since a person ordinarily skilled in the art can readily implement a wide variety of attachment mechanisms to achieve the desired coupling functions described herein.

FIG. 2 also illustrates another feature of the embodiment in which the edge of an end of the outer-shaft tube 1 may be turned inwardly so as to rotatably retain a control ball such, for example, as the control ball 6.

FIG. 3 is an end view of the manipulator arm 10 of an embodiment of the present invention. The figure illustrates the various rotational and pivotal movements of a control ball (see arrow 25). In theory, the pivot angle of control balls 6 and 8 are limited only by the type of bedding on the outer-shaft tube 1.

Figure 4:
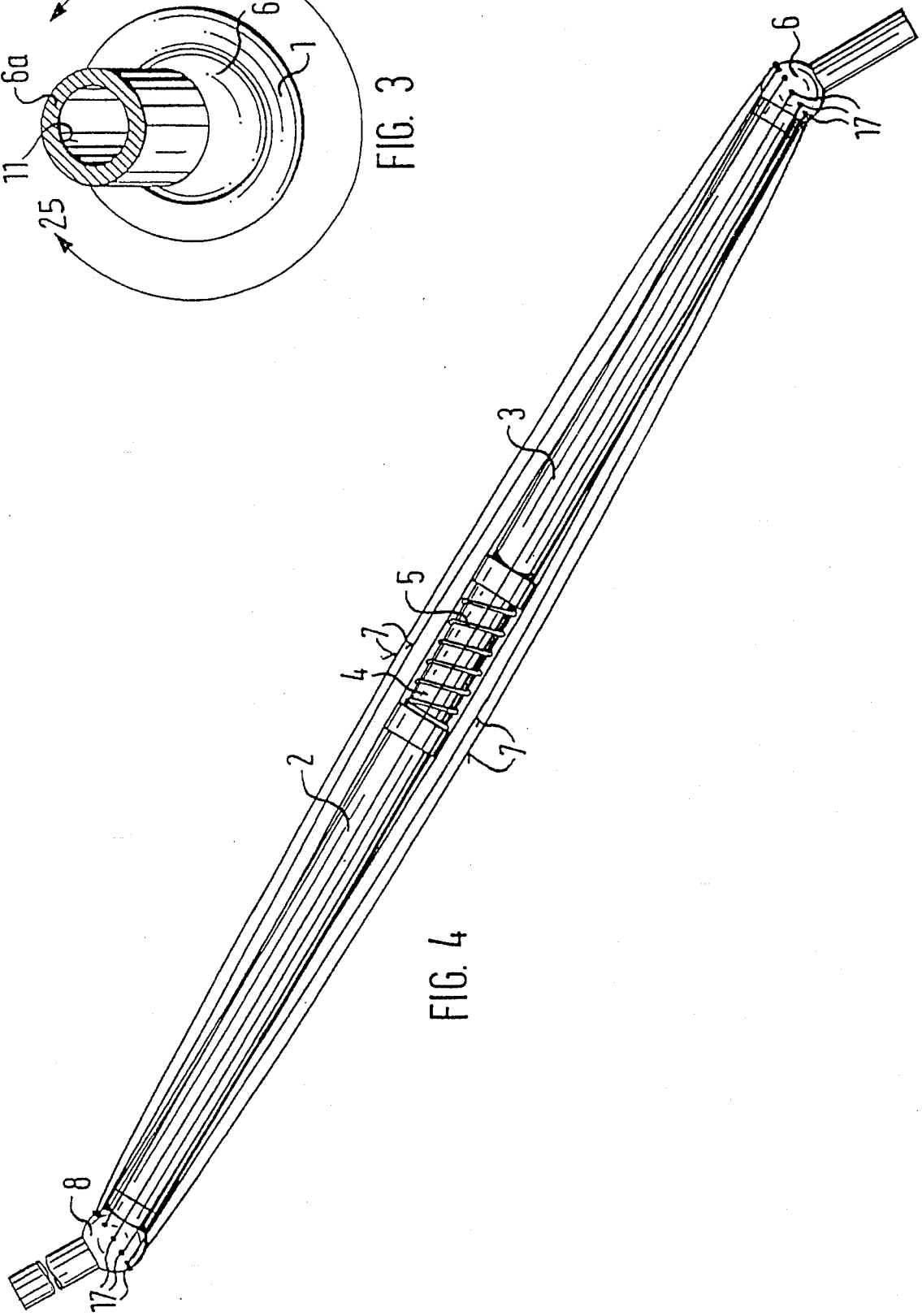
FIG. 4 is a side view of the manipulator arm of FIG. 1 without the outer-shaft tube.

FIG. 4 shows the manipulator arm 10 without the outer-shaft tube 1 thereby exposing the various internal components such, for example, as the non-positive connection of the two control balls 6 and 8. The control wires 7, as shown in FIG. 4, are pre-tensioned by resilient means such, for example, as the coil spring 5 so that the wires 7 remain taut irrespective of the rotational or pivotal positions of the control balls 6, 8. Attachment points 17 for the control wires 7 are preferably arranged equidistantly and circularly on the peripheral surface of the control balls 6 and 8. Guidance for the control wires 7 may be provided by forming longitudinal recesses along the peripheral surfaces of outer spacer tubes 2, 3 or additionally, inner spacer tube 4.

Figure 5:
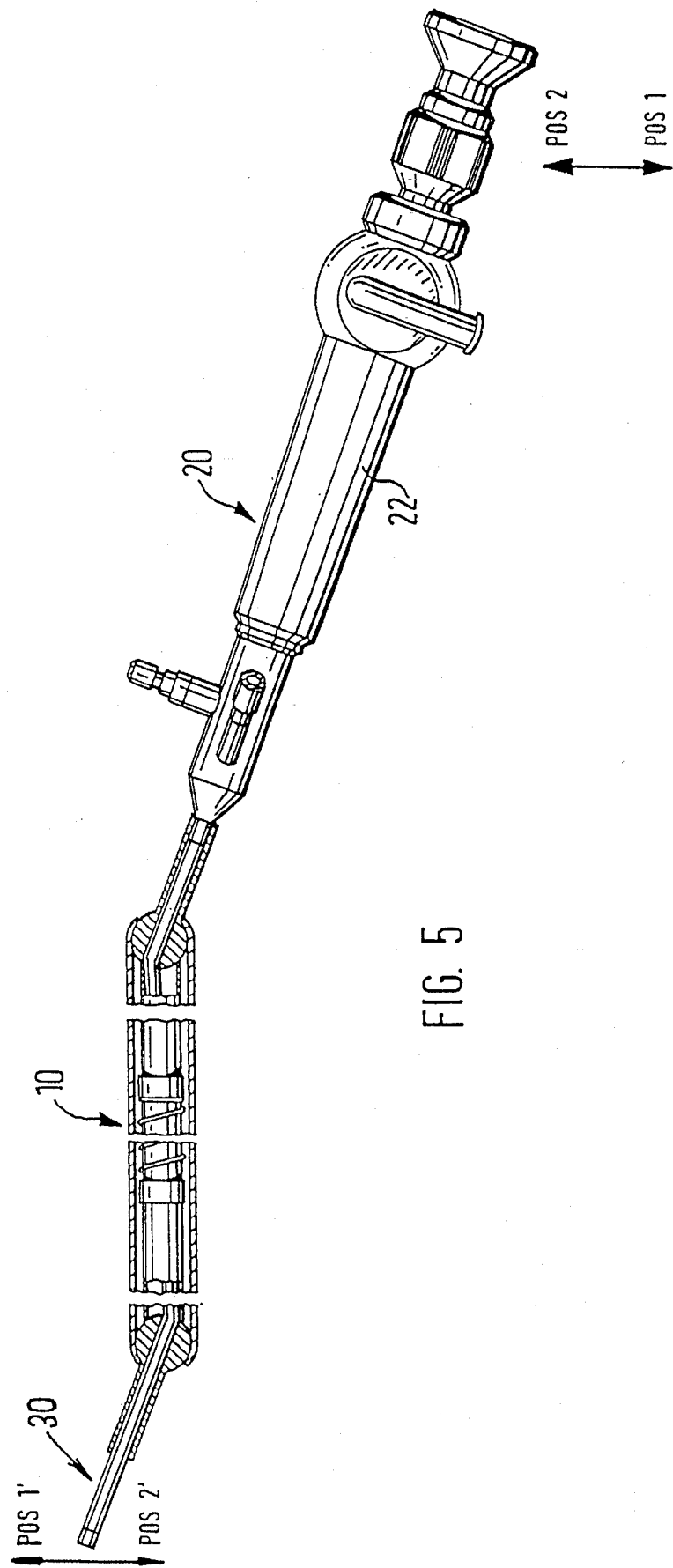
FIG. 5 is a side sectional view of the manipulator of FIG. 1 with an exemplary flexible endoscope attached.

Finally, FIG. 5 shows another application of the manipulator arm 10. As is illustrated, a handling part 20 such, for example, as a flexible endoscope 22 can be easily interfaced with the manipulator arm 10. Thus, with the aid of the manipulator arm 10, a user can accurately manipulate an effector part 30 of the flexible endoscope 22 within a bodily cavity for visual examination.

It is evident that given the requirement for pre-tensioned control wires 7, every rotational and pivotal movement of the proximal control ball 6 can be accurately transmitted in a non-positive fashion and without play to the distal control ball 8. In FIG. 1, the two double arrows, respectively designated as POS 1-POS 2 and POS 1'-POS 2', illustrate that pivotal movements of the handling part 20 at the proximal end of the manipulator arm 10 cause corresponding pivotal movements of the effector part 30 at the distal end.

Although the drawings show the two control balls 6 and 8 to be of substantially the same diameter, other combinations of diameters are of course possible. For example, if it is desired that the control ball 6 at the proximal end has a larger diameter than that of the control ball 8 at the distal end, then pivoting and rotational movements of control ball 8 relative to control ball 6 are proportional to the ratio of the diameters of the two control balls 6, 8. It will readily be appreciated by a person ordinarily skilled in the art that in this particular embodiment, large angular movements caused by the handling part 20 will lead to relatively small angular movements of the effector part 30.

In operation, pivoting actions imparted to the handling part 20 are directly and correspondingly transmitted to the effector part 30 of an instrument. The manipulator arm 10 enables a user to advantageously manipulate a flexible device as though the instrument is a standard, non-hinged medical device such, for example, as a flexible forceps or endoscope. Though not specifically shown, it is advantageous for the outer shaft tube 1 of the manipulator arm 10 be set in a cannula similar to the way a trocar is set.

The preferred embodiments of the manipulator arm 10 according to the invention discussed above and depicted in the drawings have been described in relation to surgical instruments. However, it is self-evident that the manipulator arm 10, in accordance with the present invention, can also be employed for non-medical applications such, for example, as manipulations and examinations in enclosed spaces.

In sum, the manipulator arm 10 according to the invention enables a user to perform operations and examinations in enclosed spaces such, for example, as bodily cavities. It does so by permitting a user to initiate movements at the handling part 20 and thereby maneuver an effector part 30 of an instrument selectively and detachably secured to the distal end of the manipulator arm 10. Moreover, the manipulator arm 10 is advantageously light, simply constructed and can be produced economically.

It is further contemplated that a close-coupled-device (CCD) sensor may be installed in the distal control ball 12 for transmission of images via electrical or optical signals communicating through the proximal control ball 6. The signals can then be received by a signal converter and/or transmitted to an external controller.

Furthermore, instead of manually manipulating the handling part 20, a motorized device can be used to automate movements of the distal control ball 12 by selectively engaging the proximal control ball 6.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, however, therefore, to be limited only as indicated by the scope of the claims appended hereto.

What is claimed is:

1. A manipulator arm for maneuvering an instrument having an effector part and a handling part, comprising:

an outer-shaft tube having a proximal end, a distal end and a bore therethrough;

a first control ball being disposed rotatably and pivotably at said proximal end of said outer-shaft tube, said first control ball having actuating means for selectively and detachably connecting the handling part of the instrument to said first control ball;

a second control ball being disposed rotatably and pivotably at said distal end of said outer-shaft tube, said second control ball having following means for selectively and detachably connecting the effector part of the instrument to said second control ball; and coupling means disposed in said outer-shaft tube for coupling said first control ball to said second control ball so that rotational and pivotal movements of said first and second control balls are correspondingly transmitted to each other.

2. The manipulator arm as recited in claim 1, wherein said coupling means forms a non-positive mechanical connection between said first and second control balls.

3. The manipulator arm as recited in claim 1, wherein said first and second control balls and said coupling means have a bore therethrough forming a connecting passage from said actuating means, through said coupling means to said following means.

4. The manipulator arm as recited in claim 3, wherein said arm is configured to receive an at least partially flexible shaft of said instrument through said bore.

5. The manipulator arm as recited in claim 3, wherein said coupling means comprises a plurality of control wires with each end of each said control wire attached to the respective peripheral surface of said first and second control balls.

6. The manipulator arm as recited in claim 5, wherein said plurality of control wires are substantially equidistantly spaced on the peripheral surface of said control balls.

7. The manipulator arm as recited in claim 5, wherein said coupling means further comprises plural spacer tubes arranged between said first and second control balls, said plural spacer tubes being selectively positioned within and slidably movable along a longitudinal direction of said outer-shaft tube so as to hold said first and second control balls at said proximal and distal ends of said outer-shaft tube, respectively.

8. The manipulator arm as recited in claim 7, wherein said plural spacer tubes comprise a first outer spacer tube, a second outer spacer tube, and an inner spacer tube, said first outer spacer tube being disposed proximate said first control ball, said second outer spacer tube being disposed proximate said second control ball, said inner spacer tube being positioned annularly within said first and second outer spacer tubes for slideable movement therewithin.

9. The manipulator arm as recited in claim 8, further comprising a coil spring interposed between confronting ends of said first and second outer spacer tubes and slidably received over said inner spacer tube so that said first and second outer spacer tubes are resiliently urged against said first and second control balls.

10. The manipulator arm as recited in claim 9, wherein said first and second outer spacer tubes further comprise guidance means for guiding said control wires.

11. The manipulator arm as recited in claim 9, wherein said first and second outer spacer tubes and said inner spacer tube further comprise guidance means for guiding said control wires.

12. The manipulator arm as recited in claim 11, wherein said guidance means comprises substantially equidistant and longitudinally extending peripheral recesses on said first and second outer spacer tubes.

13. The manipulator arm as recited in claim 11, wherein said guidance means comprises substantially equidistant and longitudinally extending peripheral recesses on said first and second outer spacer tubes and said inner spacer tube.

14. The manipulator arm as recited in claim 1, wherein said actuating means comprises an actuator portion.

15. The manipulator arm as recited in claim 14, wherein said actuator portion is shaped as a tube.

16. The manipulator arm as recited in claim 1, wherein said following means comprises a follower portion.

17. The manipulator arm as recited in claim 16, wherein said follower portion is shaped as a tube.

* * * * *